United States Patent
Spinelli et al.

(10) Patent No.: US 6,694,970 B2
(45) Date of Patent: Feb. 24, 2004

(54) ADHESIVE STRIP FOR OPENING NASAL PASSAGES

(75) Inventors: Thomas Spinelli, East Northport, NY (US); Jahangir S. Rastegar, Stony Brook, NY (US)

(73) Assignee: Omnitek Partners LLC, Bayshore, NY (US)

( * ) Notice: Subject to any disclaimer, the term of this patent is extended or adjusted under 35 U.S.C. 154(b) by 0 days.

(21) Appl. No.: 10/338,494

(22) Filed: Jan. 8, 2003

(65) Prior Publication Data
US 2003/0150449 A1 Aug. 14, 2003

Related U.S. Application Data
(60) Provisional application No. 60/346,551, filed on Jan. 8, 2002.

(51) Int. Cl.[7] ............... A61M 15/00; A61M 16/00; A62B 7/00
(52) U.S. Cl. ............... 128/200.24; 128/848; 606/199; 606/204.45
(58) Field of Search ............... 128/848, 200.24, 128/857, 858, 912, DIG. 26; 602/12, 13, 14, 15, 16, 17, 60, 61, 74, 46, 47, 902, 41, 42, 43, 54, 58, 55, 56, 57, 62; 606/191, 196, 199, 201, 204.15, 204.45

(56) References Cited

U.S. PATENT DOCUMENTS

| | | | | |
|---|---|---|---|---|
| 5,913,873 A | * | 6/1999 | Blach et al. | 606/204.45 |
| 5,931,854 A | * | 8/1999 | Dillon | 606/204.45 |
| 5,967,126 A | * | 10/1999 | Ofner | 123/525 |
| 6,270,512 B1 | * | 8/2001 | Rittmann | 606/199 |
| 6,325,772 B1 | * | 12/2001 | Scheuermann et al. | 602/22 |
| 6,336,456 B1 | * | 1/2002 | Ruben | 128/206.19 |
| 6,352,548 B1 | * | 3/2002 | Blach et al. | 606/199 |

* cited by examiner

*Primary Examiner*—Weilun Lo
*Assistant Examiner*—Michael Mendoza

(57) ABSTRACT

A device for opening nasal passages is provided. The device including: a strip of material having an adhesive on one surface thereof for applying the strip across a human nose; at least one biasing member attached or embedded in the strip, the at least one biasing member being fabricated from a material which exhibits a shape memory effect upon being heated toward a human body temperature, the at least one biasing member having a shape upon being heated toward the human body temperature which biases the nasal passages of the human nose toward an open position. In a variation of the device, the strip itself is at least partly fabricated from the material. In another variation, the shape memory material is replaced with a biasing material, which does not need the application of heat to bias the nasal passages open, such as spring steel or a resilient thermoplastic.

11 Claims, 2 Drawing Sheets

ADHESIVE STRIP FOR OPENING NASAL PASSAGES

CROSS REFERNCE TO RELATED APPLICATION

This application claims the benefit of U.S. Provisional Application 60/346,551 filed on Jan. 8, 2002, the entire contents of which is incorporated herein by its reference.

FIELD OF THE INVENTION

The present invention relates generally to adhesive strips for opening nasal passages, and more particularly, to an adhesive strip for opening nasal passages having a shape memory biasing member which biases the nasal passages of the human nose toward an open position.

PRIOR ART

Adhesive strips for opening nasal passages are known in the art. Such strips are generally fabricated from a woven material and have an adhesive specially formulated for adhering to human skin on one surface thereof. When adhered to the nose, the strips generally have some biasing effect to bias the nasal passages open. However, the biasing effect of adhesive nose strips of the prior art exhibit very little biasing effect and therefore do not adequately open nasal passages.

SUMMARY OF THE INVENTION

Therefore it is an object of the present invention to provide a device for opening nasal passages, which overcomes the problems of similar devices of the prior art.

Accordingly, a device for opening nasal passages is provided. The device comprises: a strip of material having an adhesive on one surface thereof for applying the strip across a human nose; at least one biasing member attached or embedded in the strip, the at least one biasing member being fabricated from a material which exhibits a shape memory effect upon being heated toward a human body temperature, the at least one biasing member having a shape upon being heated toward the human body temperature which biases the nasal passages of the human nose toward an open position.

The strip of material preferably comprises at least two layers where the at least one biasing member is disposed in between the two layers. Alternatively, the at least one biasing member is adhered to the surface of the strip of material. The strip of material is fabricated from a woven fabric.

The biasing member material is preferably a shape memory metal. Alternatively, the biasing member material is a shape memory plastic.

In a variation of the device for opening nasal passages, the device comprises: a strip of material having an adhesive on one surface thereof for applying the strip across a human nose, the strip at least partially being fabricated from a material which exhibits a shape memory effect upon being heated toward a human body temperature, the strip having a shape upon being heated toward the human body temperature which biases the nasal passages of the human nose toward an open position.

Preferably, the material is a shape memory metal. Alternatively, the material is a shape memory plastic.

In another variation, the device comprises: a strip of material having an adhesive on one surface thereof for applying the strip across a human nose; at least one biasing member attached or embedded in the strip, the at least one biasing member having a shape which biases the nasal passages of the human nose toward an open position.

Preferably, the biasing member is fabricated from spring steel. Alternatively, the biasing member is fabricated from a thermoplastic.

In yet another variation, the device comprises: a strip of material having an adhesive on one surface thereof for applying the strip across a human nose, the strip having a shape which biases the nasal passages of the human nose toward an open position.

Preferably, the biasing member is fabricated from spring steel. Alternatively, the biasing member is fabricated from a thermoplastic.

Also provided is a method for opening nasal passages. The method comprises: applying an adhesive strip to a human nose, the adhesive strip being or having a biasing member at least partially fabricated from a material which exhibits a shape memory effect upon being heated toward a human body temperature, the strip having a shape upon being heated toward the human body temperature which biases the nasal passages of the human nose toward an open position; heating the biasing member toward the human body temperature; and biasing the nasal passages toward an open position.

Still yet provided is a method for opening nasal passages. The method comprises: applying an adhesive strip to a human nose, the strip having a shape upon being heated to the human body temperature which biases the nasal passages of the human nose toward an open position; and biasing the nasal passages toward an open position.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of biasing materials, it has been found particularly useful in the environment of shape memory materials. Therefore, without limiting the applicability of the invention to biasing members fabricated from shape memory materials, the invention will be described in such environment. Those skilled in the art will appreciate that spring materials may also be used, as is described below.

Figure 1:
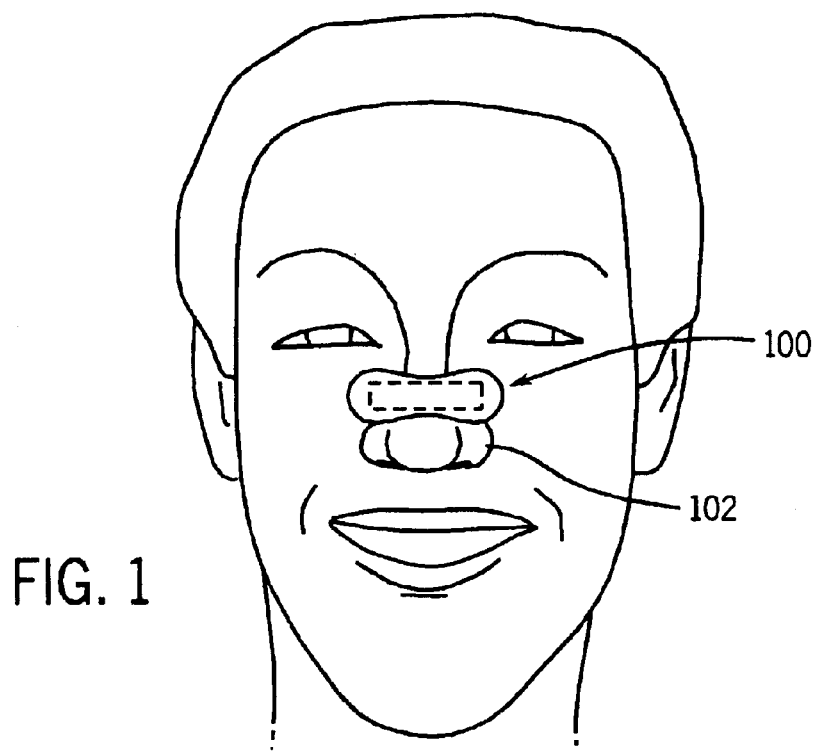
FIG. 1 illustrates the device of the present invention adhered to the nose of a human.
Figure 2:
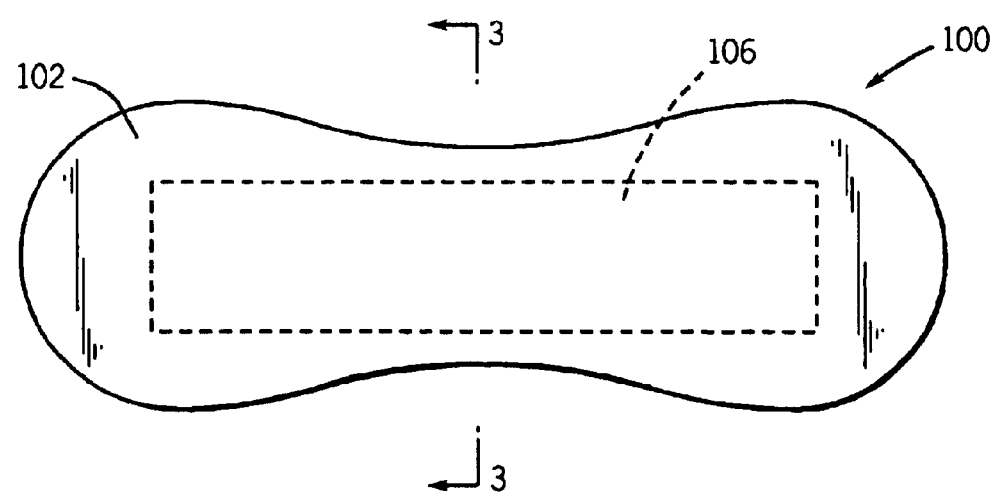
FIG. 2 illustrates a front view of a preferred implementation of the device of the present invention.

Referring now to FIGS. 1 through 4, a device for opening nasal passages is illustrated therein, the device being generally referred to by reference numeral 100. The device 100 comprises a strip 102 of material having an adhesive on one surface 103 thereof for applying the strip 102 across a human nose 104 as is shown in FIG. 1. The use of adhesive strips for the nose is well known in the art as is the adhesive used to secure such to human skin, such as the facial skin of the nose.

The device 100 also includes at least one biasing member 106 attached or embedded in the strip 102. In a first embodiment of the device of the present invention, the at least one biasing member 106 is preferably fabricated from a material which exhibits a shape memory effect upon being heated toward a human body temperature. The at least one biasing member 106 also has a shape upon being heated toward the human body temperature which biases the nasal passages 108 of the human nose 102 toward an open position with a biasing force $F_B$.

Although many shape-memory materials may be used, a nickel-titanium alloy (NiTi) is suitable. One such NiTi alloy is manufactured, for example, by Shape Memory Applications, Inc., Santa Clara, Calif. In general, metallic shape-memory alloys, such as NiTi, CuZnAl, and CuAlNi alloys, undergo a transformation in their crystal structure when cooled from the high-temperature austenite form, which is generally stronger, to the low-temperature martensite form, which is weaker. When a shape-memory material is in its martensitic form, it is easily deformed to a new shape. However, when the material is heated through its transformation temperature, it reverts to austenite and recovers its previous shape with great force. The temperature at which the material reverses its high temperature form when heated can be adjusted by slight changes in material composition and through heat treatment. The shape-memory process can be made to occur over a range of a few degrees, if necessary, and the shape transition can be made to occur millions of times. Heating is preferably effected by the body heat of the nose.

Some shape-memory materials can be made to exhibit shape-memory only upon heating (one-way shape-memory), or also can undergo a shape change upon cooling (two-way shape memory). Shape-memory materials are available in many forms including, for example, wires, rods, ribbons, strips, sheets, and microtubing, and can be used to fabricate shape-memory structures having linear, planar and composite forms. Although, metals having a shape memory effect are preferred, plastics having a shape memory effect can also be used without departing from the scope or spirit of the present invention.

Figure 3A:
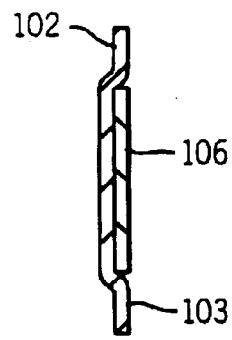
FIG. 3a illustrates a sectional view of a first variation of the device as it would appear if taken along line 3—3 of FIG. 2.
Figure 3B:
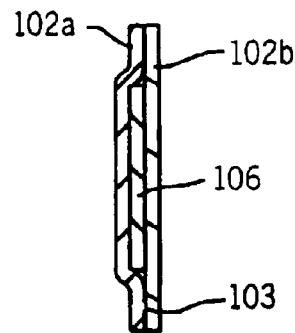
FIG. 3b illustrates a sectional view of a second variation of the device as it would appear if taken along line 3—3 of FIG. 2.
Figure 4:
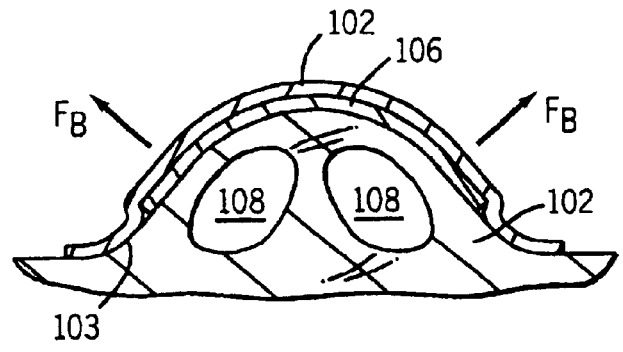
FIG. 4 illustrates a partial sectional view of the human nose having the preferred implementation of the device of the present invention adhered therein.

As shown in FIG. 3A, the strip of material 102 is preferably a single layer 2 of a bandage-type woven material, as is known in the art. The biasing member 106 preferably comprises a single thin layer which is adhered to the inner surface 103 of the strip of material 102 such that the biasing member 106 is in substantial contact with the skin of the nose 102 when adhered to the nose, as is shown in FIG. 4. The biasing member 106 can also be several strips of material, each exhibiting a shape memory effect and each being adhered to the inner surface 103 of the strip of material 102. The several biasing members can be positioned directly next to each other or can be spaced a predetermined distance from each other. Alternatively, as shown in FIG. 3B, the strip of material 102 can comprise two layers 102a, 102b wherein the biasing member 106 is disposed in between the two layers 102a, 102b.

Figure 5:
FIG. 5 illustrates a biasing member in a first shape.
Figure 6:
FIG. 6 illustrates the biasing member in a second shape.

When in it's biasing shape (i.e., after being heated through its transformation temperature), the biasing member 106 can take many shapes. Preferably, the shape is either flat as shown in FIG. 5 or curved away from the nose, as is shown in FIG. 6.

Figure 3C:
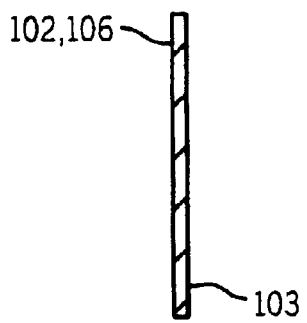
FIG. 3c illustrates a sectional view of a third variation of the device as it would appear if taken along line 3—3 of FIG. 2.

Referring now to FIG. 3C, in a variation of the first embodiment, the strip of material and the biasing member can be of a unitary design. That is, the strip of material both has an adhesive on one surface 103 for applying the strip across a human nose 102 and is at least partially fabricated from a material, which exhibits a shape memory effect upon being heated toward a human body temperature. As with the biasing member discussed above, the strip has a shape upon being heated toward the human body temperature, which biases the nasal passages of the human nose toward an open position.

In a second embodiment of the device for opening nasal passages, the device comprises strip of material 102 having an adhesive on one surface 103 thereof for applying the strip across a human nose 102 and further having at least one biasing member 106 attached or embedded in the strip. Where the at least one biasing member 106 has a shape which biases the nasal passages of the human nose toward an open position. However, in this embodiment, the biasing force of the biasing member is generated by a spring force stored in the biasing member. For instance, the biasing member can be fabricated from spring steel or a resilient thermoplastic. Therefore, the biasing member 106 would be forced to take the shape of the nose 104 when adhered to the nose by the adhesive. The biasing member would then try to return to its unbiased shape and exert a biasing force $F_B$ to open the nasal passages 108. As discussed above with regard to the variation of the first embodiment, a variation of the second embodiment would be to integrate the strip of material and biasing member into a single piece.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A device for opening nasal passages, the device comprising:
    a strip of material having an adhesive on one surface thereof for applying the strip across a human nose;
    at least one biasing member attached or embedded in the strip, the at least one biasing member being fabricated from a material which exhibits a shape memory effect upon being heated toward a human body temperature, the at least one biasing member having a shape upon being heated toward the human body temperature which biases the nasal passages of the human nose toward an open position.

2. The device of claim 1, wherein the strip of material comprises at least two layers and wherein the at least one biasing member is disposed in between the two layers.

3. The device of claim 1, wherein the biasing member material is a shape memory metal.

4. The device of claim 1, wherein the biasing member material is a shape memory plastic.

5. The device of claim 1, wherein the strip of material is fabricated from a woven fabric.

6. The device of claim 1, wherein the at least one biasing member is adhered to the surface of the strip of material.

7. A device for opening nasal passages, the device comprising:
   a strip of material having an adhesive on one surface thereof for applying the strip across a human nose, the strip at least partially being fabricated from a material which exhibits a shape memory effect upon being heated toward a human body temperature, the strip having a shape upon being heated toward the human body temperature which biases the nasal passages of the human nose toward an open position.

8. The device of claim 7, wherein the material is a shape memory metal.

9. The device of claim 7, wherein the material is a shape memory plastic.

10. A method for opening nasal passages, the method comprising:
   applying an adhesive strip to a human nose, the adhesive strip being or having a biasing member at least partially fabricated from a material which exhibits a shape memory effect upon being heated toward a human body temperature, the strip having a shape upon being heated toward the human body temperature which biases the nasal passages of the human nose toward an open position;
   heating the biasing member toward the human body temperature; and
   biasing the nasal passages toward an open position.

11. A method for opening nasal passages, the method comprising:
   applying an adhesive strip to a human nose, the strip having a shape upon being heated to the human body temperature which biases the nasal passages of the human nose toward an open position; and
   biasing the nasal passages toward an open position.

* * * * *